US00PP21354P2

(12) United States Plant Patent
White

(10) Patent No.: US PP21,354 P2
(45) Date of Patent: Oct. 5, 2010

(54) MINI-FLORA ROSE PLANT NAMED 'SAVOROCKIES'

(50) Latin Name: *Rosa hybrida*
Varietal Denomination: SAVorockies

(75) Inventor: Wendy White, Ipswich, MA (US)

(73) Assignee: Nor'East Miniature Roses, Arroyo Grande, CA (US)

( * ) Notice: Subject to any disclaimer, the term of this patent is extended or adjusted under 35 U.S.C. 154(b) by 0 days.

(21) Appl. No.: 12/456,815

(22) Filed: Jun. 22, 2009

(51) Int. Cl.
*A01H 5/00* (2006.01)

(52) U.S. Cl. ..... Plt./120

(58) Field of Classification Search ..... Plt./120
See application file for complete search history.

*Primary Examiner*—Annette H Para

(57) ABSTRACT

'SAVorockies' is a new and distinct variety of Mini-Flora rose plant noted for its strong, sweet fragrance, attractive, fully double flowers, and above average disease resistance. Flowers of various shades of apricot-pink last well on the plant. A mature plant can be almost constantly in bloom during the growing season.

1 Drawing Sheet

Genus and species: *Rosa hybrida.*
Varietal denomination: 'SAVorockies'.

CROSS REFERENCE

This current invention is a bushy and upright growing variety of rose plant of the Mini-Flora Class. With its apricot-pink, double flowers it closely resembles 'SAVapam' (U.S. Plant Pat. No. 17,329), the pollen parent of this new invention and from this same breeding program. Though flowers are very similar in color and form, they are easily distinguished, as noted in Table 1 below.

| | New Invention - 'SAVorockies' | 'SAVapam' |
|---|---|---|
| Flower Color | Apricot-Pink with russet tones of Scarlet, azalea-pink and Shell-pink, in the newly opening flower, | Pink Blend, various shades including Shell-pink, Orient-pink and Salmon-pink. |
| Aging Properties of Flowers | Gradually loses all the yellow tone in the flower petals before they drop from the plant, leaving only pink and white with a red blush. | Retains the yellow in the coloring so it finishes more of a peachy-pink; petals do not take on a blush. |
| Flower Form | Generally there are 32 to 36 petals. Starts with flat upper profile, which gradually becomes somewhat arched. | Generally there are 27 to 32 petals. Upper profile is flat from opening to fade. |
| Fragrance | Strong | Moderate |

BACKGROUND OF THE INVENTION

This new invention relates to a new and distinct variety of hardy, bush type plant of the Mini-Flora rose class. This variety was developed by myself, Wendy R. White, under controlled conditions in a greenhouse in Rowley, Mass., by crossing the following two rose cultivars:

an unnamed and unintroduced seedling from this same breeding program as seed parent 'SAVapam' as pollen parent.

The new plant was selected as a seedling in the mid-winter of 2003. In the fall of 2003, it was shipped to Arroyo Grande, Calif. where it was grown in a plastic covered greenhouse for 6 years, before being moved outside in December of 2008. In April of 2009, it was shipped to Ipswich, Mass. where it continues growing outside in a large 5 gallon plastic bucket.

The idyllic goals of this breeding program were to create unique diminutive roses with the qualities of disease resistance, hardiness, and having fragrant, hybrid-tea form blooms, born in abundance from late spring through late fall. The cultivar chosen as seed parent was a rose of the miniature class and had very fragrant flowers, born in abundance. The cultivar chosen as pollen parent is a Mini-Flora rose with moderate fragrance and is known for its vigor, hardiness and excellent disease resistance. The resulting new cultivar is a prolific bloomer and has a strong fragrance, similar to that of its seed parent, and is a Mini-Flora rose with vigor, hardiness and disease resistance almost as good as its pollen parent.

Comparison between the new invention and its parents is shown in Table 2.

| New Invention - 'SAVorockies' | Seed Parent - Seedling | Pollen Parent - 'SAVapam' |
|---|---|---|
| Of the Mini-Flora rose class | Of the miniature rose class | Of the Mini-Flora rose class |
| Flowers of apricot-pink with russet tones; gradually losing all yellow tonality. | Lavender-pink colored flowers. | Flowers of various shades of a pink blend: including shell-pink, Orient-pink and salmon-pink. |
| 32-36 petals | 15-18 petals | 27-32 petals |
| Strong fragrance | Strong fragrance | Moderate fragrance |
| Height of 22 to 34 inches | Height of 15 to 18 inches | Height of 26 to 32 inches. |
| Petals age some before eventually dropping cleanly | Petals age considerably and drop after an extended period of time | Petals drop from the fading bloom, promptly and cleanly |

BRIEF SUMMARY OF THE INVENTION

This present invention relates to a new distinct variety of hardy, bush type rose plant of the Mini-Flora class. The characteristics distinguishing it from its parents and from all other varieties of which I am aware are its unique combination of pink blend, double flowers, averaging 2¾ inches across, having hybrid tea form, and a strong, sweet fragrance. The variety is further characterized by:

an abundance of these flowers borne singly, and in loose sprays of single-borne and small-cluster borne flowers flowers opening slowly and lasting a long time on the plant dark green, semi-glossy foliage a plant with above average disease resistance a plant that is suitable for soft wood production in pots a plant that grows and blooms satisfactorily both in the greenhouse and outdoors, providing fragrant decoration in the garden as a specimen plant, as a low hedge, or in large containers

BRIEF DESCRIPTION OF THE DRAWING

The accompanying color photograph, taken in May, is an image of a plant of this new invention, growing in a container in an artificial soil mix. In this image buds and flowers can be seen in different stages of development. Old and new growth may also be seen (much of the oldest foliage dropped when the plant was allowed to become too dry but there are plenty of mature leaves visible).

BOTANICAL DESCRIPTION OF THE PLANT

Unless otherwise noted, the following observations, measurements, values and comparisons describe this 6-year-old plant of *Rosa hybrida* 'SAVorockies', of the Mini-Flora rose class. The plant was grown in artificial soil-mix in a plastic covered greenhouse for 6 years, before being moved outside in Arroyo Grande, Calif. in December of 2008. In April of 2009, it was shipped to Ipswich, Mass. where it has been kept outside, except for brief protection from unaccustomed cold. The detailed description is presented below in outline format. Color references are made using The Royal Horticultural Society Colour Chart, except where common terms of color are used.

FLOWERS

Blooming habit: Flowers open slowly; fast repeat.

Borne: Initially singly; then on long stems in loose sprays of 5 or more, flowers are borne singly and occasionally in small clusters of 2 or 3; on shorter stems in loose sprays of 3 to 5.

Bud: Broadly ovate, most often 17/32 inch long and 15/32 inch wide, varying between 31/64 and 35/64 inch long and 28/64 and 33/64 inch wide before the sepals divide.

Sepals: (These observations were taken from mature flowers after the petals had dropped.) Permanently attached to the receptacle, rolling back to or almost to the stem as the flower opens, moving slightly away from the stem as the hip forms and matures.

*Size.*—Extend beyond the tip of the bud by 15/32 to 27/32 inch, the longer lengths on the larger buds, which are usually borne singly. Widths are most commonly 11/32 and 12/32 inch, varying from 11/32 to 13/32 inch; lengths vary from 29/32 to 1 4/32 inches, averaging about 1 inch.

*Color.*—Outer surface: outer sepals near 138A; inner sepals between 138A and 143A with the centers flushed heavily with a reddish-purple, between 175A and 187A. Inner surfaces are near 160B in the center and between 137B and 147B bordering the margins.

*Texture.*—Outer surface — semi-glossy, becoming matte, especially along the margins, as they mature; stipitate glands dot the surfaces, varying in quantity from few to many, and usually in parallel rows; on the inner sepals they are found mostly down the center of the surface with few or none toward the margins. Texture inner surface — fine pubescence.

*Shape.*—Outer sepals are acuminate with acicular apices. Inner sepals are ovate.

*Margins.*—Outer sepals have one to four foliar appendages along each margin and entirely lined with stipitate glands that are tipped with a dark Cardinal Red, near 53A. Inner sepals have ciliate margins and no foliar appendages.

Receptacle:

*Form.*—Conical.

*Color.*—Medium yellow-green, between 144B and 144A, lightly flushed on the sunward side with near 187A; as it matures the cyanine coloring disappears.

*Surface.*—Glabrous, becoming slightly pubescent toward the peduncle.

*Diameter.*—3/16 inch where it connects to the peduncle, becoming 7/16 inch where it connects to the receptacle.

Bloom:

*Size when fully expanded.*—Width varies from 2 7/16 to 3 1/16 inches, and not symmetrically round by 2/16 to 3/16 inch. Depths vary from 1 5/16 to 2 inches, with depth relative to diameter.

*Form.*—Begins with a flattened upper profile, which gradually becomes arcuate and flattened again when full open. Lower profile begins cupped and becomes convex.

*Petal counts.*—Varied from 25 to 41 with 1 to 11 petaloids, petaloid counts are not relative to petal counts.

*Fragrance.*—Strong, sweet.

*Lasting time on plant.*—2 weeks or more from opening bud to full open bloom.

Petals:

*Arrangement.*—Imbricated.

*Thickness.*—Medium with excellent substance.

*Texture.*—Satiny surfaces, both adaxial and abaxial.

*Size of outermost petals on the full open bloom.*—Widths varied from 1 7/32 to 1 12/32 inches. Lengths varied from 1 4/32 to 1 11/32.

*Shape.*—Outer petals are oblate to broadly spatulate with arcuate margins, curling under forming an apparent triangle; apices are acute most often with a notch on each side, sometimes causing the margin to be ruffled; bases are broadly obtuse. Intermediate petals are spatulate, with rounded margins that may be entire, and elliptical bases. Inner petals are obovate, with broadly oval margins and cordate bases; apices are similar to those on the outer petals but are less pronounced.

Petals — color:

*General tonality.*—Apricot-pink blend; general tonality from a distance — Light apricot-pink and dark apricot-pink bicolor.

*When sepals first divide.*—A red between 43B and 45D.

*During the first few days.*—Outer petals. Upper surface is Claret Rose, near 50B along margins, gradually blending into a Scarlet Red, near 43D, and becoming a deep Lemon Yellow, near 13A, at base and point of attachment; there may be streaks of white, near 157C, or of very light green, near 147C, along the main and other veins. Reverse is mostly near 43C with streaks of the colors seen when the sepals first divided; basal area is a lighter yellow between 18B and 14D; point of attachment is a Chartreuse Green near 154C. Inner petals. Upper surface is lighter, a Shell Pink between 37B and 38B, with basal area and point of attachment near 13B. Reverse is near 43D, with basal area and point of attachment a light Primrose Yellow near 4C.

Petals—variable colors: It seems a well-fertilized plant shows more yellow tones. As the blooms open, nutrition plays a noticeable role in the hues of the blooms.

*With lower nutrient levels.*—The outer five petals become more pink, a Neyron Rose near 55B on both surfaces, with outer edges near 55A. Intermediate petals are a bit lighter, near 55C. Inner petals show yellow tones and are Peach, near 29D, with near 43B along the margins.

*When grown at higher nutrient levels.*—The five outer petals are more of a Jasper Red, between 39C and 39B, with outer edges flushed red, between 46D and 46C. Other petals are a light Peach near 29D and are more of an Apricot-Peach towards the center of the bloom; outer edges may be flushed with 46D. As the blooms continue to open more of the area along the margins becomes flushed with the darker colors; the yellow tones begin to fade away.

*On full blown blooms most of the yellow tones are gone.*—First full open blooms were observed with outer petals of a very light French Rose between 49D and 155A and edges were a Venetian Pink near 49C, blushed with between 52C and 58C, with basal area near 11D and point of attachment near 8C; the reverse appeared near 55C with basal area near 155D and point of attachment near 4C; Intermediate petals were a Carmine Rose near 52C with near 58C on the outer edges and all surfaces exposed to the sun; the basal area was whiter than 155D and point of attachment was a very light yellow, near 158A; the reverse appeared near 52D, with basal area near 158A and point of attachment near 2D. Inner petals — same coloring as intermediate petals except with basal area near 155D and point of attachment near 158C on the upper surface and basal area near 155D and point of attachment near 158D on the reverse.

*Later in the season, after additions of fertilizer, colors were noted somewhat darker in the full blown blooms.*—Outer petals, upper surface was noted between 49D and 49C with edges lightly flushed with near 59A, Ruby Red, and basal area and point of attachment near 1D; reverse may be a very pale pink, near 56C, with a deep Rhodonite Red, near 51A, along the margins, and a basal area and point of attachment near 1D; Also noted on another bloom on the same plant on the same day: the upper surface was near 56C, near 51A along the margins, with the basal area and point of attachment were near 2C; the reverse was noted as near 49C, flushed a bit lighter, between 52B and 51A, with veins near 56D, no discernible basal area and point of attachment was near 1D.

*As the bloom continues to age.*—Petal surfaces continue to lighten and blushing intensifies on areas exposed to the sun, to a medium red near 45D, 52D or somewhere in between, being darkest along the edges and blending into the near white of the petals with streaks and freckles.

Petaloids:

*Color.*—Same as the inner petals.

*Shape.*—Deformed petals from cleft to only half a petal with the main vein along one margin, and bases may be as narrow as to be considered stipes.

*Size.*—Widths were measured from 10/32 to 22/32 inch and lengths were measured from 11/32 to 1 2/32 inches.

REPRODUCTIVE ORGANS

Androecium:

*Stamens.*—Regularly arranged inside and adjacent to the perianth, Quantity — numerous, usually between 130 and 160.

*Filaments.*—Length — about 3/16 inch. The top is Cadmium Orange, near 23A; the middle is suffused with Indian Orange, near 32A; the base is a translucent white.

*Anthers.*—Color — near 23A.

Gynoecium:

*Pistils.*—Originate in the center of top of the receptacle. Quantity — about half as many as stamens.

*Styles.*—Thin, curving or undulating slightly. Translucent, white at the base, cherry red near the top.

*Stigmas.*—Translucent, near white.

Hips: Mature hips not observed.

*Shape.*—Enlarging hypanthium indicate the form will be pear-shape. Seeds were starting to protrude from the top of some of the forming hips.

PLANT

Habit: Upright, well and uniformly branched. Flowers held above plant canopy. Flowers borne initially singly; as buds develop, long flowering stems initiate from nodes below the bud, forming loose sprays; each flowing stem within the spray usually bears one bud, occasionally a small cluster of 2 or 3; in turn, as buds develop on the lowest stems in these sprays, flowering stems initiate from nodes beneath them. New canes originates from the base at the ground.

Growth: Vigorous growth.

*Healthy.*—Very good resistance to blackspot, downy mildew and rust; above average resistance to powdery mildew.

*Height.*—Of 22 to 34 inches.

*Width.*—Of 24 to 34 inches.

*Root initiation from cuttings.*—3 to 7 days.

Foliage: Pinnately compound with 5 -7 leaflets, occasionally 3.

*Size.*—Mature leaf — 4 5/8 to 5 7/8 inches, regardless of number of leaflets. Mature terminal leaflet — 1 11/16 to 2 1/4 inches long, 1 3/32 to 1 3/8 inches wide.

*Shape.*—Narrow ovate with acute apices and oval bases.

*Appearance.*—Upper surface — semi-glossy, main vein entirely recessed and primary lateral veins noticeably recessed, decreasing toward the margin. Lower surface — matte, main vein protrudes entirely, primary lateral veins protruding somewhat, decreasing toward the margins.

*Texture.*—Upper surface — glabrous. Lower surface — glabrous when young, becoming slightly leathery when mature.

*Margins.*—Fine and near even serration.

Foliage—color:

*New foliage.*—Upper surface — anthocyanin coloration is strong, margins near 187A; surface begins near 137C or 137D flushed with near 187A; as degree of flushing lessens, the green darkens to near 147A. Lower surface — near 137D, flushing with near 187C is lighter and in sporadic areas.

*Old foliage.*—Anthocyanin coloring is absent. Upper surface is darker than between 147A and 136A. Lower surface — near 147B.

Petioles:

*Length.*—Varies from 11/16 to 1 3/16 inches, not relative to leaf length.

*Girth.*—Uniformly 3/32 inch.

*Color on young leaf.*—Upper surface — near 187A along the ridge; near 183A in the grooves. Lower surface — near 187D.

*Color on old leaf.*—Upper surface — as leaflet surface, darker than between 147A and 136A. Lower surface — between 146D and 144B.

Rachis:

*Color.*—Same as petioles.

*Length.*—9/16 to 1 25/64 inches.

*Girth.*—5/64 inch at the base, usually tapering to 3/64 inch toward the terminal leaflet.

Petiolules:

*Color.*—Same as petioles.

*Length.*—To terminal leaflet — Varying from 12/16 to 15/16 inch. Petiolules to basal leaflets — varying from 3/32 to 7/32 inch. Petiolules to other leaflets — varying from 5/64 to 7/64 and lengths in a pair often differing by up to 1/32 inch.

Stipules: Paired at the base of each petiole. Lengths vary from 10/32 to 15/32 inch attached and 5/32 to 9/32 inch angled outward, most often, at 45° from the petiole. Lengths within each pair may differ by none to 3/32 inch. Margins appear entire and ciliate.

*Color.*—The same as the ridges of the petiole which they are attached.

Wood:

*Color.*—New wood — a medium green, near 137C. Old wood — darker, between 137A and 147B.

*Texture.*—New wood — glabrous; semi-glossy. Old wood — usually glabrous.

*Main canes.*—Diameters at the base varied from 15/32 to 22/32 inch. On young plants less than one year old. Diameters of main canes varied from 7/32 to 9/32 inch. Main canes may have 15 nodes.

*Flowering stems.*—Diameters at the base were 5/32 to 6/32 inch, tapering to 4/32 inch toward the pedicel, and increasing by 1/64 inch to attach to the pedicel. Lengths depend how far down they originate, varying from 2 to 9 inches.

Pedicel:

*Color.*—Scheele's Green, near 144B, flushed on the sunward side with near near 178A. Becomes a medium yellow-green, near 146B, as it matures and cyanine coloring disappear.

*Surface.*—Covered with fine fuzz and numerous, minute prickles.

*Length/diameter.*—On main canes and primary laterals — 2 1/8 inches long; diameter 3/16 inch below the receptacle, tapering to 2/16 connecting to the stem. On secondary laterals — 1 6/8-1 7/8 inches long; diameter 4/32 inch below the receptacle, tapering to 3/32 connecting to the stem. On tertiary laterals — 1 5/8 inches long; diameter 9/64-8/64 inch below the receptacle, tapering to 7/64 connecting to the stem.

Lenticels: Begin forming in the 3$^{rd}$ or 4$^{th}$ year, on only one side of the canes. Run parallel, vertically, gradually increasing in width; they have not been observed to cover more than 1/5 of the total cane diameter.

*Color.*—Medium brown, near 177C.

Example of cane development: New cane originating from the base of the plant at the ground was 10 inches long to the peduncle. As the bud began to form, primary laterals began growth from the upper 8 of the 15 nodes on the cane. Before that bud opened, each primary lateral grew somewhat higher than the bud on the main cane to which it was attached, forming a large, loose spray. Diameters of primary laterals varied from 4/32 to 5/32 inch; lengths of developing primary laterals ranged from about 2 inches to about 9 inches, depending on how far down the main cane they originated. Buds on laterals that originated toward the top of the cane developed quicker than those on laterals originating lower down on the cane. The lowest two primary laterals have 3 and 5 leaflet leaves; the remainder of the laterals have only 2 and 3 leaflet leaves. The lowest two primary laterals initiated secondary laterals just as their buds begin to form. The 9 inch lateral had 8 nodes; the 6 inch lateral had 7 nodes; the remainder of the laterals, 5 inches or shorter, had 5 to 3 nodes, with quantity of nodes relative to length of the lateral. Observations of the mature plant give indication this is typical growth for this cultivar.

Prickles:

*Quantity.*—On main stalks — none. On laterals — 2 or 3 between nodes, regardless of spacing of nodes. On rachis — usually 3 on abaxial crest. On peduncle — numerous minute prickles.

*Form.*—Upper profile curves slightly or slants downward; lower profile is cowl-shaped; tapers to a point.

*Length.*—On laterals — between 6/32 and 9/32 inch. On pedicel — 1/64 to 2/64 inch.

*Color.*—When young — near 53A. On mature growth — near 177C; on mature pedicels, still near 153A.

The invention claimed is:

1. A new and distinct variety of hardy rose plant of the Mini-Flora rose class is claimed, substantially as illustrated and described, characterized particularly as to novelty by the strong sweet fragrance, the distinctive coloring of its blooms, the lasting quality of its blooms on the plant, and its above average resistance to diseases.

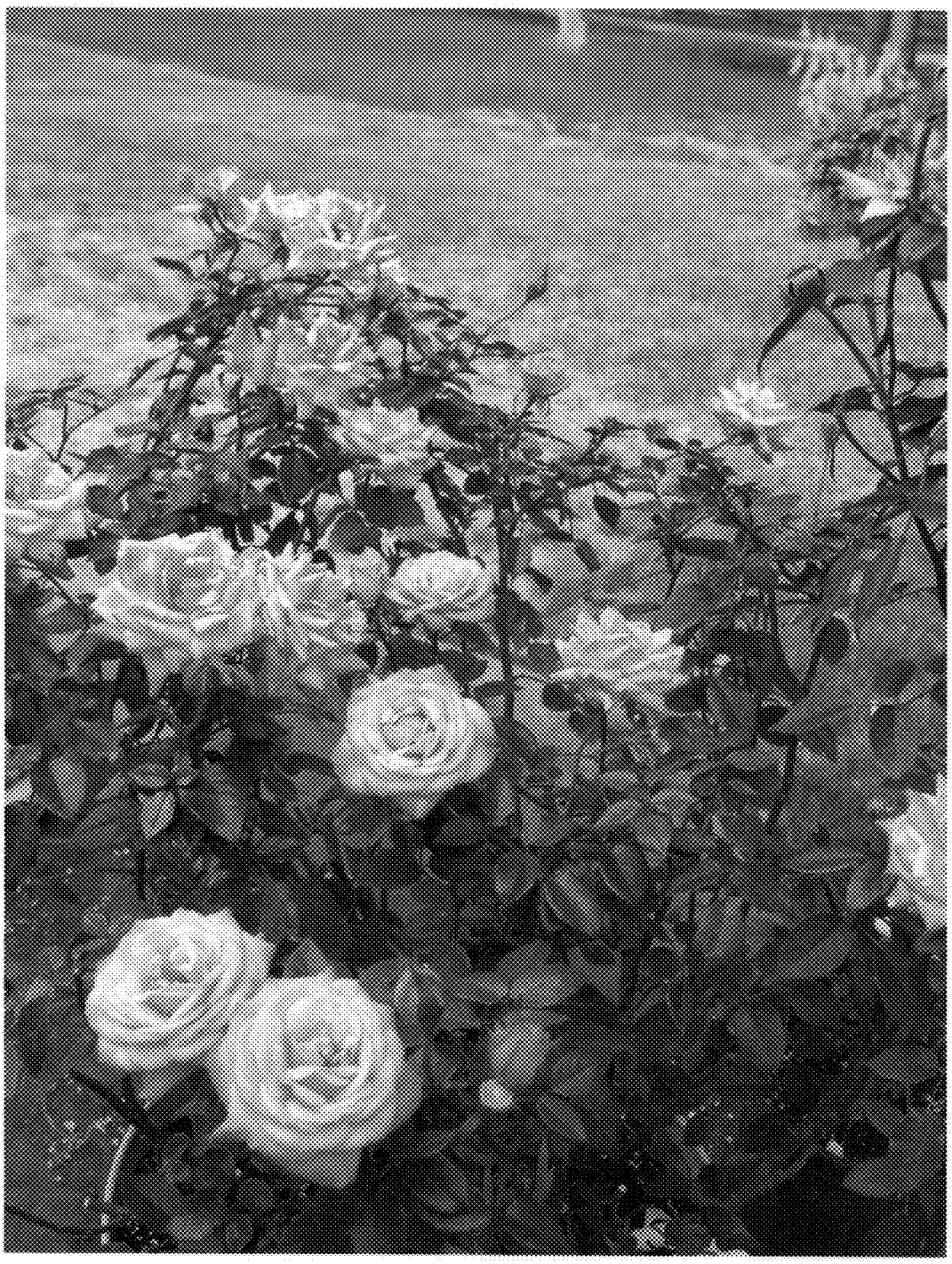

* * * * *